United States Patent
Vignon et al.

(10) Patent No.: US 10,130,330 B2
(45) Date of Patent: *Nov. 20, 2018

(54) ULTRASONIC TRACKING OF ULTRASOUND TRANSDUCER(S) ABOARD AN INTERVENTIONAL TOOL

(71) Applicant: KONINKLIJKE PHILIPS N.V., Eindhoven (NL)

(72) Inventors: Francois Guy Gerard Marie Vignon, Cambridge, MA (US); William Tao Shi, Cambridge, MA (US); Jean-Luc Robert, Cambridge, MA (US); Ameet Kumar Jain, Cambridge, MA (US); Luis Felipe Gutierrez, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/450,755

(22) Filed: Mar. 6, 2017

(65) Prior Publication Data
US 2017/0172539 A1  Jun. 22, 2017

Related U.S. Application Data

(63) Continuation of application No. 14/958,355, filed on Dec. 3, 2015, now Pat. No. 9,585,628, which is a
(Continued)

(51) Int. Cl.
*A61B 8/00* (2006.01)
*A61B 8/08* (2006.01)
(Continued)

(52) U.S. Cl.
CPC ............ *A61B 8/0841* (2013.01); *A61B 8/12* (2013.01); *A61B 8/4488* (2013.01); *A61B 8/483* (2013.01);
(Continued)

(58) Field of Classification Search
CPC ..... A61B 8/0841; A61B 8/483; A61B 8/4488; A61B 8/12; A61B 8/5207; G01S 15/8993; G01S 15/8997; G01S 7/52085
See application file for complete search history.

(56) References Cited

U.S. PATENT DOCUMENTS

| 4,249,539 A | 2/1981 | Vilkomerson |
| 4,401,124 A | 8/1983 | Guess |

(Continued)

FOREIGN PATENT DOCUMENTS

| EP | 1245191 A2 | 10/2002 |
| JP | 10277040 A | 10/1998 |

(Continued)

OTHER PUBLICATIONS

Frazier, Catherine H. et al "Synthetic Aperture Techniques with a Virtual Source Element" IEEE Transactions on Ultrasonics, Ferroelectrics, and Frequency Cotnrol, vol. 45, No. 1, Jan. 1998, pp. 196-207.

(Continued)

*Primary Examiner* — Joel Lamprecht

(57) ABSTRACT

In one aspect, an ultrasound receive beamformer is configured for one-way only beamforming of transmissive ultrasound using one-way delays. The receive beamforming in some embodiments is used to track, in real time, a catheter, needle or other surgical tool within an image of a region of interest. The tool can have embedded at its tip a small ultrasound transmitter or receiver for transmitting or receiving the transmissive ultrasound. Optionally, additional transducers are fixed along the tool to provide the orientation of the tool.

10 Claims, 7 Drawing Sheets

Related U.S. Application Data continuation of application No. 13/643,374, filed as application No. PCT/IB2011/051729 on Apr. 20, 2011, now Pat. No. 9,282,946.

(60) Provisional application No. 61/330,641, filed on May 3, 2010.

(51) Int. Cl.
*A61B 34/20* (2016.01)
*A61B 8/12* (2006.01)
*G01S 7/52* (2006.01)
*G01S 15/89* (2006.01)
*A61B 90/00* (2016.01)

(52) U.S. Cl.
CPC ............ *A61B 8/5207* (2013.01); *A61B 34/20* (2016.02); *G01S 7/52085* (2013.01); *G01S 15/8915* (2013.01); *G01S 15/8993* (2013.01); *G01S 15/8997* (2013.01); *A61B 2090/3782* (2016.02)

(56) References Cited

U.S. PATENT DOCUMENTS

| | | |
|---|---|---|
| 6,038,468 A | 3/2000 | Rex |
| 6,053,870 A | 4/2000 | Fulton |
| 6,120,453 A | 9/2000 | Sharp |
| 6,506,156 B1 | 1/2003 | Jones |
| 6,587,709 B2 | 7/2003 | Solf |
| 9,282,946 B2 * | 3/2016 | Vignon ............... A61B 8/0841 |
| 9,585,628 B2 * | 3/2017 | Vignon ............... A61B 8/0841 |
| 2002/0173720 A1 | 11/2002 | Seo |
| 2003/0060700 A1 * | 3/2003 | Solf ..................... A61B 8/0833 600/411 |
| 2007/0213616 A1 * | 9/2007 | Anderson ............ A61B 8/0833 600/448 |
| 2009/0069692 A1 | 3/2009 | Cooley |
| 2009/0069693 A1 | 3/2009 | Burcher |
| 2009/0099456 A1 | 4/2009 | Burcher |
| 2009/0182235 A1 | 7/2009 | Robert |
| 2014/0121502 A1 * | 5/2014 | Vignon ................ A61B 8/0841 600/424 |

FOREIGN PATENT DOCUMENTS

| | | |
|---|---|---|
| JP | 11076241 A | 3/1999 |
| JP | 2001299756 A | 10/2011 |

OTHER PUBLICATIONS

Nikolov, Svetoslav Inanov et al "Precision of Needle Tip Localization using a Receiver in the Needle", IEEE International Ultrasonics Symposium Proceedings, 2008, pp. 479-482.

* cited by examiner

ULTRASONIC TRACKING OF ULTRASOUND TRANSDUCER(S) ABOARD AN INTERVENTIONAL TOOL

CROSS-REFERENCE TO PRIOR APPLICATIONS

This application is a Continuation application of U.S. Ser. No. 14/958,355, filed on Dec. 3, 2015, now U.S. Pat. No. 9,585,628, which will issue on Mar. 7, 2017, which is a Continuation application of U.S. Ser. No. 13/643,374, filed on Oct. 25, 2012, now U.S. Pat. No. 9,282,946, issued on Mar. 15, 2016, which is the U.S. National Stage application under 35 U.S.C. § 371 of International Application No. PCT/IB2011/051729, filed on Apr. 20, 2011, which claims the benefit of U.S. Provisional Patent Application No. 61/330,641, filed on May 3, 2010. These applications are hereby incorporated by reference herein.

FIELD OF THE INVENTION

The present invention is directed to one-way only beamforming of transmissive ultrasound and, more particularly, to using such beamforming for tracking an interventional tool during real-time imaging.

BACKGROUND OF THE INVENTION

Precise visualization of catheters and real-time knowledge of their localization with respect to the anatomy are needed for minimally invasive interventions. Intra-operative ultrasound is often used for these purposes. However, many surgical tools are difficult to image with conventional pulse-echo ultrasound. For instance, the usability of 3D Transoesophagial Echocardiography (3D-TEE) for guidance of catheter cardiac interventions is still limited because it is challenging to image catheters reliably with ultrasound. Catheters are specular reflectors that reflect the sound away from the imaging probe if the insonifying angles are not favorable. As a consequence, a catheter appears on and off on 3D-TEE images during its progression through the cardiac chambers. It also frequently happens that some parts of the catheter are visible and others not depending on the local angle between the catheter and the imaging beams, for instance the distal end of the catheter may be invisible and some point along its shaft may be mistaken as its tip. Also, due to weak reflection, signal from the catheter may be drowned in signal from the surrounding anatomy.

Electromagnetic (EM) tracking sensors have been mounted aboard catheters for tracking their tip and other selected locations along their shaft. However, the positioning accuracy of such sensors can get really poor (of the order of 10 mm) in EM distorted operating environment. Additionally, an independent EM tracking system adds to the equipment cost and clutter in the catheter laboratory.

U.S. Pat. No. 4,249,539, entitled "Ultrasound needle tip localization system," to D. H. R. Vilkomerson et al. (hereinafter "Vilkomerson") discloses an active ultrasound transducer that is attached at the tip of a biopsy needle to be imaged by a B-mode ultrasound scanner. The transducer at the tip of the needle, upon sensing signals from the imaging probe, immediately transmits back a short pulse. The ultrasound transducer on the needle thus merely acts as a "super-reflector" that re-radiates a strong ultrasonic signal upon insonification. The imaging paradigm is not modified and the "super-reflector" is simply seen as a very bright point in the ultrasound image. Furthermore, all embodiments described in that patent results in a very bad lateral resolution of the needle tip because there is no proper transmit focusing.

SUMMARY OF THE INVENTION

In one aspect, the present invention is directed to an ultrasonic tracking device and method for reliably determining both the position (particularly, of the tip) and orientation of a catheter or other surgical tool (e.g., a biopsy needle) relatively to the surrounding anatomy, in three dimensions and in real time. One or more small ultrasound transducers, serving as sources or receivers, are placed (embedded) at known locations on the catheter or surgical tool.

In the case of the ultrasound receiver, its 3D position can be obtained by beamforming the signals received by it as the ultrasound beams sweep the field of view during pulse-echo acquisition. In accordance with this technique, the ultrasound scanner scans using synthetic aperture with virtual transducers. The effect is to allow sensitive and specific catheter imaging, with perfect accuracy and the same resolution as that of the ultrasound imaging scanner at the same depth.

In other embodiments, in which to ultrasound transducer(s) can be either transmitters or receivers, tracking and pulse-echo image acquisition are separated by means of frequency or by means of timing (e.g., alternating, or otherwise interspersing, imaging frame with tracking frames). For example, such a transmitter, in the case of timing separation, may be triggered active in transmit by the line or frame trigger of an ultrasound scanner that temporarily interrupts its pulse-echo imaging of the medium of interest. Propagation of sound then occurs from the transmitter to the individual elements of the imaging array. The transmitter can be precisely imaged by adjusting the ultrasound scanner's beamforming delays to account for the one-way only propagation of transmissive ultrasound between the tracked ultrasound transmitter and the imaging array.

"Transmissive ultrasound," as this term is used herein, refers to ultrasound that has not reflected back for processing, in contrast to the ultrasound echoes processed in pulse-echo imaging. With respect to aspects of what is proposed herein, transmissive ultrasound is emitted from the transmitter for reception by an ultrasound scanner for those embodiments having a transmitter, and is emitted by the scanner for reception by the receiver for those embodiments having a receiver.

"One-way only" receive beamforming or "one-way" receive beamforming is, as the term is used herein, receive beamforming that uses "one-way" beamforming delays. "One-way" beamforming delays are, as the term is used herein, beamforming delays that account for the duration of ultrasound propagation toward the transducer based upon whose output the beamforming is performed. This is in contrast to "two-way" or "pulse-echo" beamforming which uses two-way delays, i.e., a delay for the pulse and a delay for the echo. With respect to aspects of what is proposed herein, the transducer, based upon whose output the beamforming is performed, is the ultrasound scanner for those embodiments having a transmitter, and is the receiver for those embodiments having a receiver.

In accordance with an aspect of the present invention, an ultrasound receive beamformer is configured for one-way only beamforming of transmissive ultrasound using one-way delays.

In accordance with a related aspect, the ultrasound receive beamformer is configured for three-dimensional imaging.

In a further aspect, an ultrasound device comprising the beamformer is configured for interspersing acquisition of imaging frames, upon which two-way beamforming is performed, with acquisition of tracking frames, upon which the one-way only beamforming is performed.

In accordance with another related aspect, the ultrasound receive beamformer is configured to, by the beamforming, localize an object within a region of interest.

In yet another aspect, for an ultrasound device comprising the beamformer, the object is an ultrasound transducer serving as a source of the transmissive ultrasound.

In a yet further aspect, the ultrasound device is configured for an ultrasound scanner triggering, by a line trigger or by a frame trigger, emission of sound from the source and/or for the source triggering the scanner active for image acquisition.

As another, related version, for an ultrasound device comprising the ultrasound receive beamformer, hardware that senses ultrasound for performing the one-way only beamforming is that which senses ultrasound used in pulse-echo imaging of the region of interest.

In one further aspect, an ultrasound device includes an ultrasound receive beamformer, hardware that senses ultrasound for performing the one-way only beamforming being separate, and physically apart from, that which senses ultrasound for performing receive beamforming used in pulse-echo imaging of the region of interest.

As a yet further aspect, an ultrasound device comprises the ultrasound receive beamformer, and a plurality of tracking transducers that includes the object within the region of interest, each of the plurality serving as a source, or each serving as a receiver, of the transmissive ultrasound, each being attached to an interventional tool. The plural tracking transducers are located mutually apart for real-time determination, by the device, of an orientation of the tool. Ones, if any, of the plural tracking transducers that serve as a source are configured for emitting signals that allow them to be distinguishable from each other.

In an alternative aspect, an ultrasound device comprises the beamformer configured for real-time tracking.

In another aspect, the ultrasound device is configured for superimposing, in real time, tracking frames on imaging frames.

In one other aspect, ultrasound for creating said tracking frames is issued by a synthetic aperture technique.

In a yet further aspect, the ultrasound device is configured for superimposing, on an imaging frame, a tracking frame having a different color map.

In some versions, the ultrasound device further comprises an ultrasound receiver subject to the real-time tracking.

In particular versions, the ultrasound receive beamformer is configured as a retrospective dynamic transmit (RDT) receive beamformer for the one-way only beamforming, the transmissive ultrasound being issued by synthetic aperture with virtual transducers.

In a related aspect, an ultrasound device comprises the RDT receive beamformer, an ultrasound transducer and an ultrasound scanner, the transducer serving as a receiver of the transmissive ultrasound and being disposed within a region of interest subject to imaging by the scanner.

As one other aspect, a method for receive beamforming of transmissive ultrasound includes configuring a receive beamformer for one-way only beamforming of the transmissive ultrasound using one-way delays.

In an additional aspect, the method further comprises one or both of:
configuring into different frequencies the transmissive ultrasound and pulse-echo ultrasound; and
alternating acquisition of imaging frames with acquisition of tracking frames.

In a different, but related, aspect, a device configured for localizing at least one of an ultrasound transmitter and an ultrasound receiver, disposed within a region of interest, is configured for:
issuing transmissive ultrasound from at least one of:
the transmitter to an ultrasound scanner for imaging the region of interest; and
the scanner to the receiver; and
one-way only beamforming the received transmissive ultrasound which, from pulse-echo imaging ultrasound, is separate by frequency or by timing, or which is issued by synthetic aperture with virtual transducers.

In a further, related version, an ultrasound device is configured for, automatically and without user intervention, calculating, with respect to an ultrasound scanner, an imaging depth of an ultrasound receiver, for switching transmit focal depth to the imaging depth, and for issuing imaging beams with that imaging depth as their focal depth. The device is further configured for using output of the receiver to localize the receiver.

Details of the novel ultrasonic tracking device and method are set forth further below, with the aid of the following drawings, which are not drawn to scale.

DETAILED DESCRIPTION OF EMBODIMENTS

Figure 1:
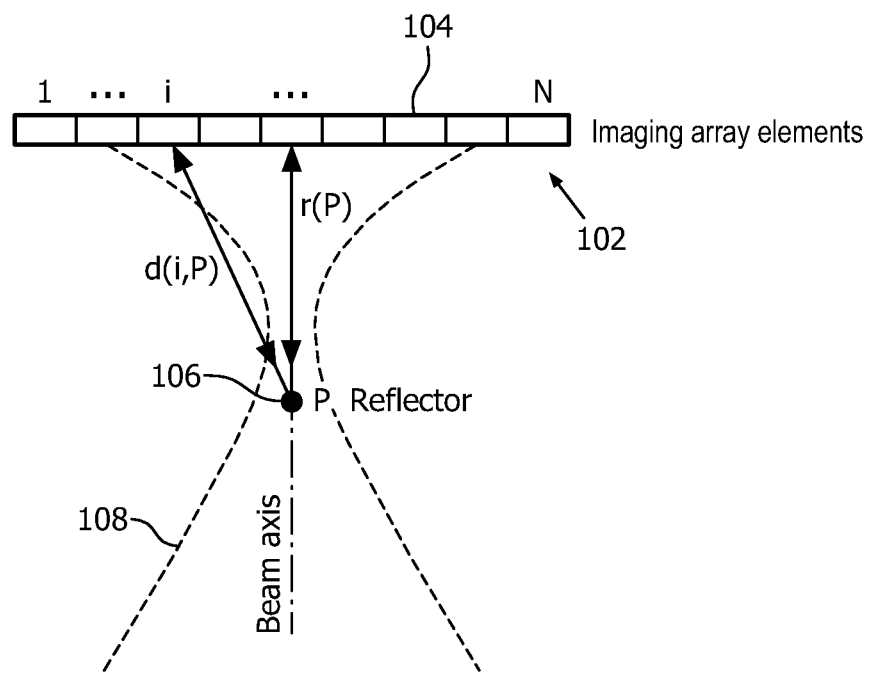
FIG. 1 is a conceptual diagram offering a comparison between two-way beamforming and one-way only beamforming.
Figure 1:
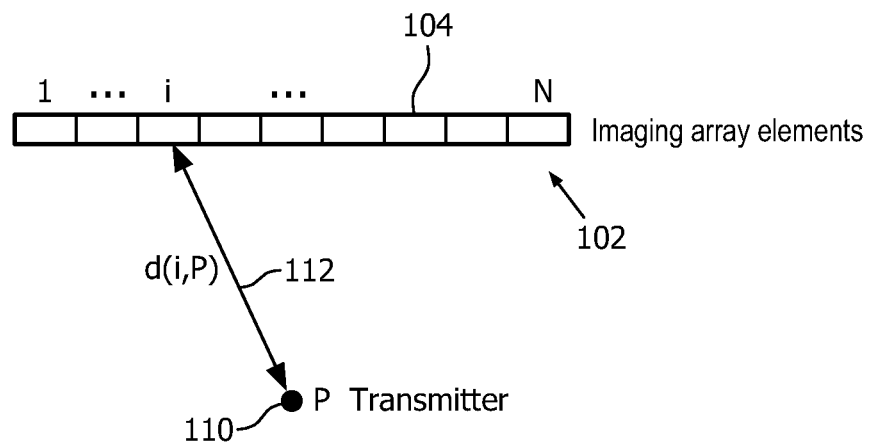

FIG. 1 offers, by way of illustrative and non-limitative example, a comparison between two-way beamforming and one-way only beamforming. The top figure, representative of two-way beamforming shows an imaging array 102 of N elements 104 issuing ultrasound that impinges on a reflector 106. Since the ultrasound waves go out and back (from the imaging array to the reflectors and back to the imaging array), we talk of "two-way" or "round-trip" beamforming. On receive (of the ultrasound that has reflected back), beamforming determines the reflectivity of the reflector 106 and the position of the reflector relative to the array 102. The array 102 send out a beam 108 that reflects off reflector 106 and returns to all elements 104 of the array 102. The flight of the pulse is over a distance r(P)+d(i,P) for element i. Each element 104 measures continually the amplitude of the return ultrasound. For each element 104, the time until a maximum of that measurement, i.e., the "round-trip time of flight," is indicative of the total flight distance. Since the r(P) leg of the flight is constant, the return flight distance d(i,P) is determined. From these measurements, the relative position of the reflector 106 is computed geometrically. As to the reflectivity of the reflector 106, it can be indicated by summing the maxima over all i (i.e., over all elements 104).

As seen from the bottom figure, one-way only (receive) beamforming, there is no echo. Instead, as in the case of transmitter 110, it emits a pulse 112 which is incident on each element 104 of the array 102. The flight here, in contrast to the two-way beamforming case, is over the distance d(i,P). The time from emission of the pulse 112 until the maximum amplitude reading at an element 104 determines the value d(i,P) for that element i. Thus, the position of the transmitter 110 can be derived geometrically, and the reflectivity calculated by summing the maximum amplitude readings.

Although one-way beamforming is implementable in the time domain via delay logic, as discussed hereinabove, it can also be implemented in the frequency domain by well-known Fourier beamforming algorithms.

Figure 2:
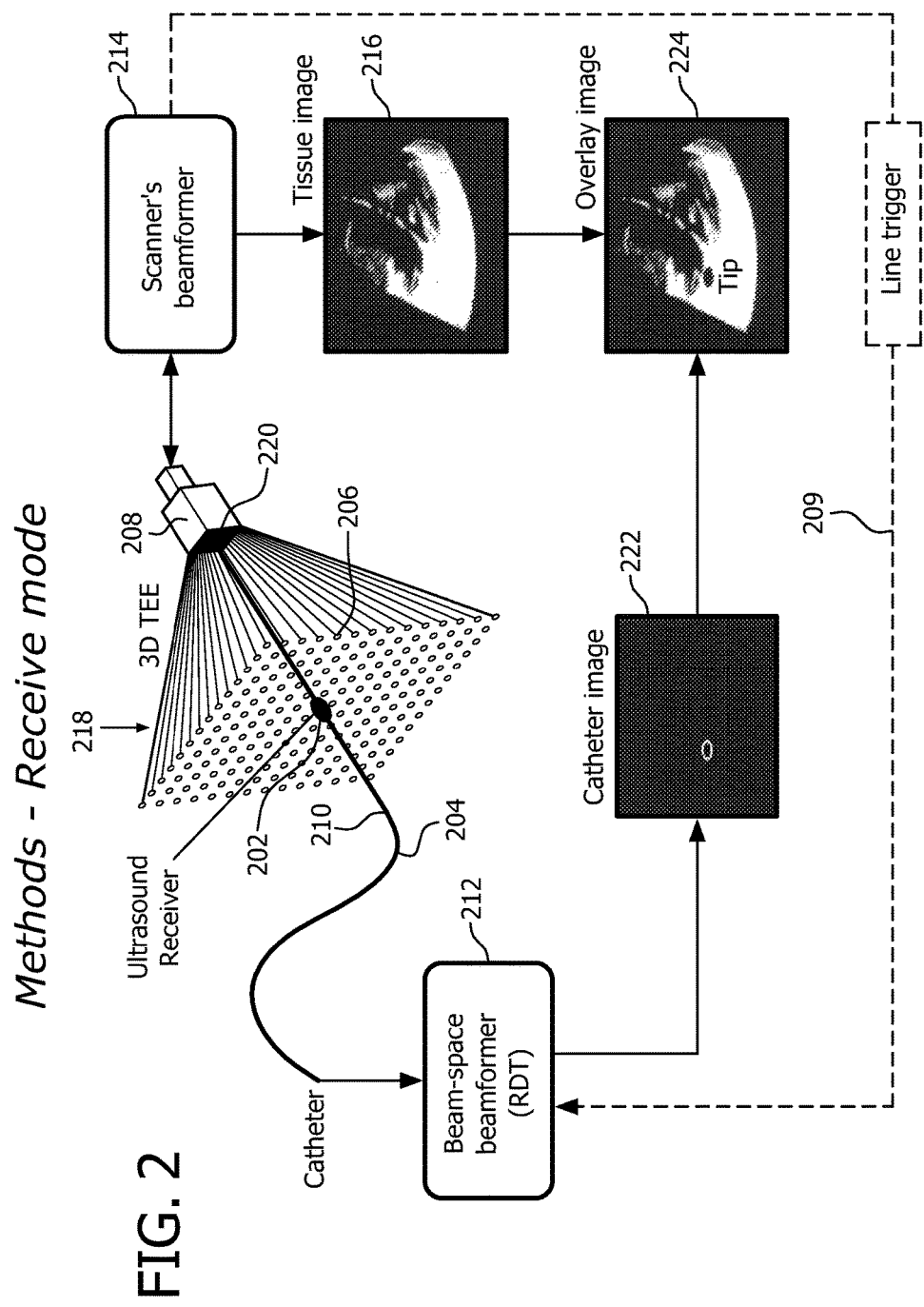
FIG. 2 is a schematic diagram depicting a configuration, which uses synthetic aperture with virtual transducers, in which a receiving ultrasound transducer fixed to a catheter is disposed within a region of interest

FIG. 2 depicts a configuration, which uses synthetic aperture with virtual transducers, in which a receiving ultrasound transducer 202, fixed to a catheter 204 (or other interventional tool or instrument, flexible or rigid), is disposed within a region of interest 206 (such as part of the heart of a patient or animal subject) which is subject to imaging by the ultrasound scanner. While the region of interest 206 is being imaged by the scanner, whose imaging probe 208 is shown in the figure, output 210 of the receiver 202 of the transmissive ultrasound is one-way only beamformed by a beam-space beamformer 212 which images using synthetic aperture with virtual transducers, i.e., a technique used in retrospective dynamic transmit focusing (RDT).

The front end of the scanner guides transmit and receive beamforming from the imaging probe 208 used, for example, in TEE (Transesophageal Echocardiography). For example, the receiver(s) 202 aboard the catheter are triggered active in receive (to, in other words, start the clock at time zero in measuring the one-way delay) by the scanner's line trigger 209 (a trigger signal is emitted each time the TEE probe emits a different transmit beam). For this purpose, an electrical connection is made to the receiver 202, such as a wired cable extending from the scanner up through the catheter 204 and to the receiver.

In practice, what is proposed herein is of particular value in three-dimensional imaging, for this and all embodiments described below.

The scanner's beamformer 214 processes the beamformed signal or display as a tissue image 216.

The signals received by the receiver(s) 202 aboard the catheter 204 are sent to the RDT beamformer 212. Moreover, hardware 218, i.e., (transducer hardware) that senses ultrasound for performing the one-way only beamforming is separate, and physically apart from, hardware 220, including, for example, transducer elements of an imaging array, which senses ultrasound for performing receive beamforming used in pulse-echo imaging of the region of interest 206.

As mentioned above, the receive beamforming is one-way only beamforming of the transmissive ultrasound using one-way delays.

Output of the RDT beamformer 212 is fed back to the back end of the ultrasound scanner for processing and displaying the resulting image 222.

Advantageously, beamforming localizes the ultrasound receiver in the region of interest 206 and yields an image of the receiver in the same coordinate system as the regular pulse-echo image of the region of interest, i.e., anatomy.

The receiver image 222 can be conveniently superimposed onto the image 216 of the anatomy, as seen in the figure from the overlay image 224, as, for example a grayscale image with full dynamic range, or, alternatively an icon representative of the image, which here is an image of the tip of the catheter 204, superimposed on the image 216 of the anatomy from the regular pulse-echo imaging sequence. With regard to an icon or predefine drawing (such as a cross or star), it can be placed at the location of maximum intensity in the tracking frame 222. If the icon is given, for example, a solid color, its color map is constant at that color; whereas, the underlying image of anatomy has a different color map corresponding, for example, to the grayscale used.

In particular, the dynamic range of the tracking frames 222 is ideally half that of the imaging frames 216 to take into account one-way beamforming only that induces sidelobes roughly twice as high as conventional two-way imaging. The tracking frames 222 are superimposed on the imaging frames 216 in real-time; they are ideally displayed with, as mentioned above, a different color. This allows unequivocal identification of the tracked device 218, and avoids saturation of the brightness image with potentially very strong signals received from the active source (as compared to the weaker pulse-echo signals backscattered by the tissue). Optionally, the point with maximum brightness in the tracking frames is simply isolated and taken as the needle tip location. A schematic drawing of the needle tip at the calculated location can then be superimposed on the image of the anatomy. The calculated position of the tracked receiver 218 can be superimposed on the real-time intraoperative ultrasound imaging display and/or pre-operative co-registered CT or MR images. Note that, if a 2D ultrasound probe is used allowing 3D tracking of the needle or catheter 204, 3D one-way beamforming can be performed during the tracking frames 222 even if the displayed pulse-echo imaging frames are 2D for easier visualization. It allows seeing the interventional tool 204 even when it is out of the imaging plane, and knowing its position with respect to the current imaging plane, enabling tool and imaging guidance.

Alternatively, although not shown in FIG. 2, the beam-space beamformer 212 may be part of the scanner's beamformer 214, i.e., signals from the receiver(s) 202 may be fed back to the scanner with the scanner's beamformer 214, in this case, having a separate one-way only beamforming function for the fed back signals.

Figure 3:
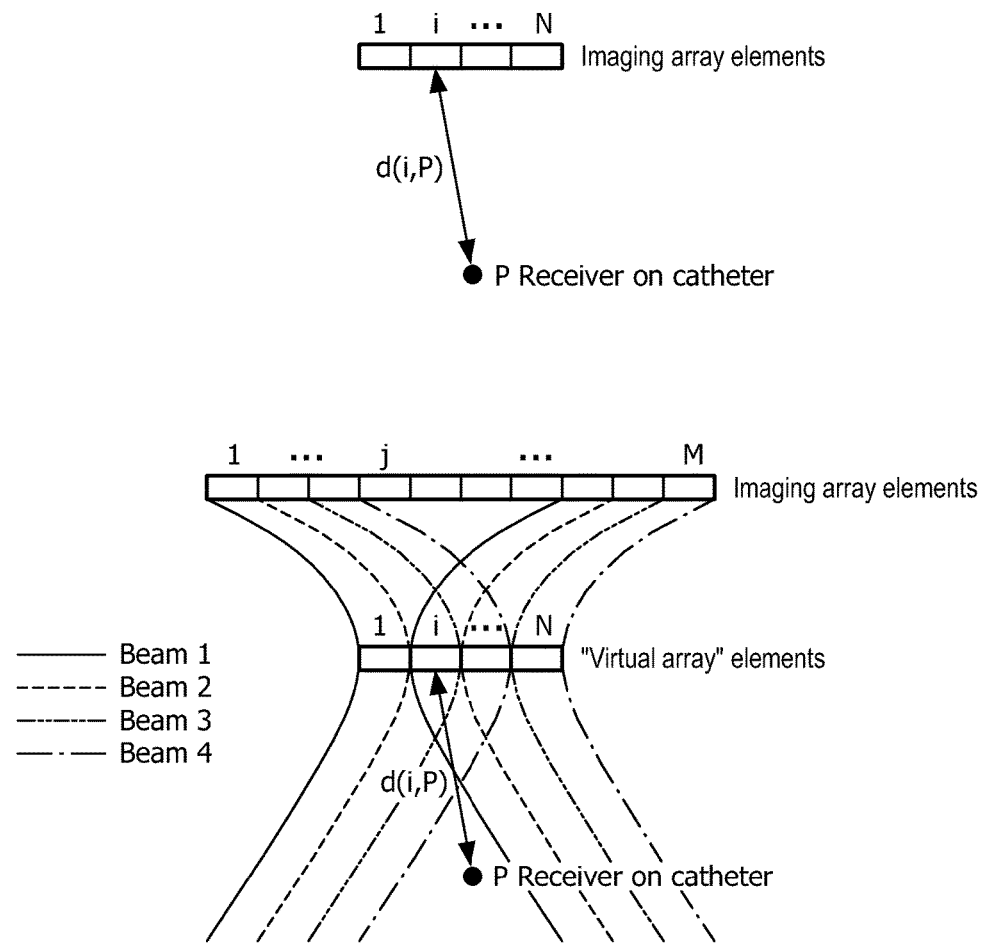
FIG. 3 is a conceptual diagram that portrays a synthetic aperture acquisition scheme in the top drawing, and the same scheme using virtual transducers in the bottom drawing.

FIG. 3 portrays a synthetic aperture acquisition scheme in the top drawing, and the same scheme using virtual transducers in the bottom drawing. Both schemes are utilized in aspects of the invention, although the one with virtual transducers (the RDT embodiment) is the one illustrated in FIG. 2.

Turning now to the top drawing in FIG. 3, the N elements of the imaging array sequentially send out an impulse, i.e., pulse, into the medium. Let $r_{i,P}(t)$ be the temporal signal received by the receiver P in the medium when element i fires an impulse. (The origin of time is taken each time an element is fired.) The travel time from i to P is $$t_{i,P} = d(i,P)/c \quad \text{(equation 1)}$$

where d(i,P) is the distance between element i and receiver P, and c is the medium's speed of sound. Thus $r_{i,P}(t)$ has its maximum at $t_{i,P}$. An image of the receiver in space is formed by, for each point Q inside the field of view, taking the summation:

$$s(Q) = \Sigma r_{i,P}(t_{i,Q}) \quad \text{(equation 2)}$$

over i=1 to N. Apodization functions may optionally be used as is standard practice in the art.

The quantity s(Q) will be maximized for Q=P; that is, at the location of the receiver.

Referring now to the bottom drawing of FIG. 3, the RDT with virtual transducers scheme is similar to above-described synthetic aperture scheme—the imaging array is replaced by a "virtual array" made of "virtual elements." Each virtual element is the focal location of one focused beam emanating from the real (physical) imaging array. There are as many virtual elements as there are focused beams from the imaging array. The imaging array sends out N beams into the medium, sweeping the field of view. Let $r_{i,P}(t)$ be the temporal signal received by the receiver P in the medium when the beam number i is fired into the medium (i.e., the virtual element i emits an impulse). The origin in time is now taken when the beam is emitted. The travel time from virtual element i to P is $$t_{i,P} = d(i,P)/c \quad \text{(equation 3)}$$

The time it takes for the transmitted beam to focus at the location of the virtual transducer is $$t_i = d(i)/c \quad \text{(equation 3)}$$

where d(i) is the distance between the center of the imaging array's active aperture and the focal point of transmit beam i (i.e., the virtual transducer i). In usual transmit schemes, all transmits are focused at the same depth, so d(i) does not depend on i; let us call it $d_1$ and $$t_1 = d_1/c \quad \text{(equation 4)}$$

It thus takes the time $t_1 + t_{i,P}$ between the emission of beam i and reception of the corresponding impulse at point P. The quantity $r_{i,P}(t)$ thus has its maximum at $t_1 + t_{i,P}$.

An image of the receiver in space is formed by, for each point Q inside the field of view, doing the summation:

$$s(Q) = \Sigma r_{i,P}(t_1 + t_{i,Q}) \quad \text{(equation 2)}$$

over i=1 to N.

The quantity s(Q) will be maximized for Q=P which is the location of the receiver.

In reality, since the virtual transducers are not punctual and have a certain directivity that is governed by the shape of the actually transmitted imaging beams, it is necessary, as known in the art, to perform some transmit beam simulations to compute the exact theoretical arrival times of each beam i at each point Q.

The RDT beamformer 212 beamforms the data received by the ultrasound receiver in beam-space (like RDT), thereby affording optimal (diffraction-limited) resolution of the tracked object at all depths.

Figure 4:
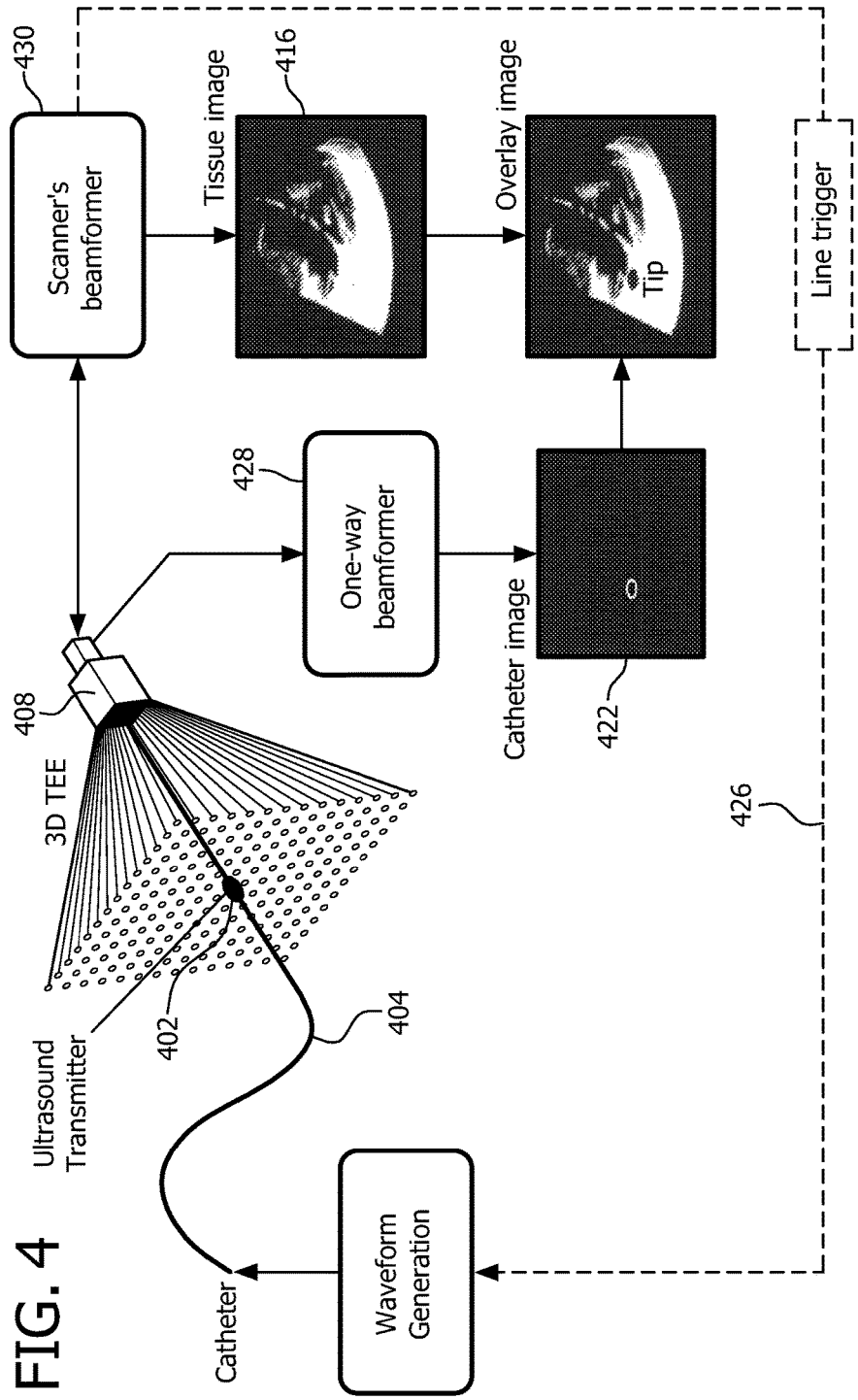
FIG. 4 is a schematic diagram showing the ultrasound transducer as a transmitter.

FIG. 4 shows the ultrasound transducer as a transmitter 402; however, the embodiments of the invention that are realizable with the transmitter are alternatively implementable with a receiver instead, such as the receiver 202 discussed above.

In order to simplify the description, it is first assume that an active source, i.e., the transmitter 402, is placed on the tracked surgical tool 404. Because of reciprocity, the active source that sends signals toward the ultrasound scanner can be replaced by an ultrasound receiver that receives signals from the ultrasound scanner, without changing the signal processing for its localization.

A small ultrasound "tracked" source, i.e., the transmitter 402, is placed at the tip of the catheter, needle or other interventional tool 404. Ideally, the tracked source 402 is as omnidirectional (monopolar radiation pattern) as possible in order to be able to sense signals from it from any direction of space. The tracked source is able to emit short pulses (optionally, more complicated waveforms with transmit codes) which ideally (but not necessarily) have a frequency band different from that of the imaging pulses of the intra-operative imaging ultrasound in order to avoid interference between the tracking and imaging pulses. Reception of tracking and imaging pulses may be differentiated either simply with receive filters or more sophisticated pulse signature identification algorithms.

The device used to sense signals from the tracked source 402 is the same ultrasonic probe 408 (ideally a 2D probe for 3D tracking) and scanner that are used to make the intra-operative ultrasound anatomical images 416.

The scanner triggers emission of sound from the tracked source 402 with its line trigger (which is designed to be fired upon emission of each beam) or frame trigger 426 (which is designed to be fired upon emission of each frame), propagation of sound then occurring from the source to the individual elements 104 of the imaging array 102.

Alternatively, the tracked source 402 can be the one that triggers image acquisition by the ultrasound scanner; this might be desirable in the case where the duty cycle and on/off times of the source on the surgical tool 404 have been optimized for best treatment safety and efficacy (in the case where the tracked source is actually used for treatment). In effect then, and ultrasound device is configured for an ultrasound scanner triggering, by a line trigger or by a frame trigger, emission of sound from the source 402 and/or for the source triggering the scanner active for image acquisition.

The most important modification that has to be made to the ultrasound scanner for tracking the source 402 is to adjust its receive beamforming delays, e.g., $[r(P)+d(i,P)]/c$ as in FIG. 1, to account for the one-way only ultrasound propagation (from the tracked source to the probe 408). In FIG. 4, this is implemented as a one-way beamformer 428 whose function is separate from the pulse-echo receive beamformer of the scanner's beamformer 430.

The ultrasound scanner alternates imaging frames (active ultrasound emission from the imaging probe 408, the tracked source 402 on the interventional tool 404 is turned off, and conventional two-way beamforming is performed for pulse-echo imaging) with tracking frames 422 (emission from the imaging probe is turned off, the tracked source on the interventional tool is turned on, one-way only beamforming is performed). Optionally, if the tracked source 402 is designed with a different frequency from the imaging frequencies, there is no need to turn on/off the tracked source/imaging probe during the imaging or tracking frames: for the tracking frames 422, the temporal receive filters are just modified to take into account the different nominal frequency of the active source.

As already mentioned, the tracked source can be replaced by a tracked receiver. In one such embodiment, the individual elements of the ultrasound scanner are turned on one by one in a synthetic aperture fashion, as explained above in connection with the top illustration in FIG. 3. As in the tracked source embodiment, imaging frames created are alternated with tracking frames created, although, unlike in the tracked source embodiment, the switching from one mode to the other cannot be foregone in favor of creating a distinction based on different frequencies.

Figure 5:
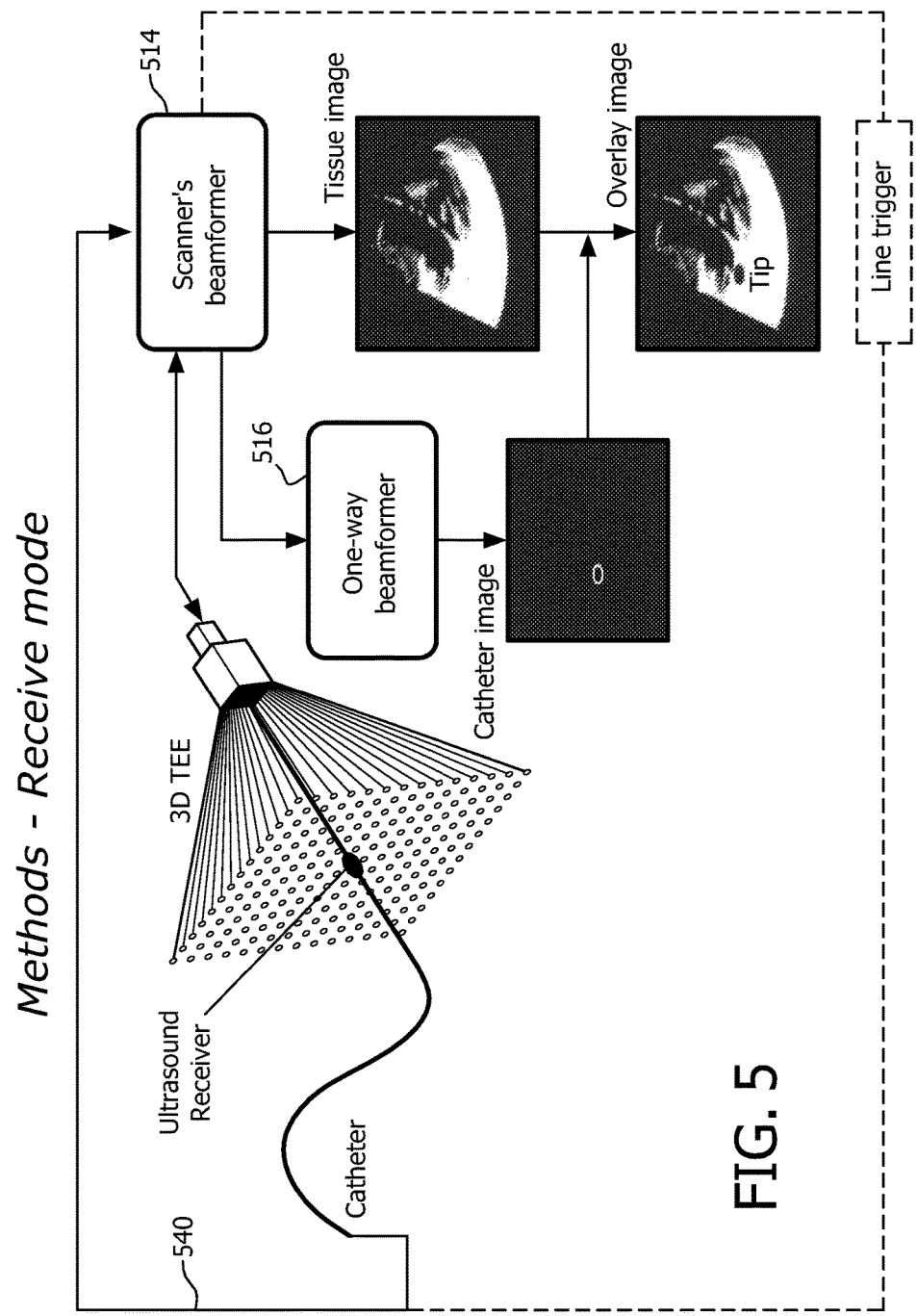
FIG. 5 is a schematic diagram showing the received signals at the tracked receiver are fed back to the ultrasound scanner's beamforming module and one-way beamforming is performed.

For the embodiment shown in FIG. 5, in which the scanner likewise transmits in synthetic aperture fashion during tracking mode, the received signals at the tracked receiver 202 are fed back, here by a wired electrical connection 540 to the ultrasound scanner's beamforming module 514, and one-way beamforming 516 is performed (due to reciprocity, signals sent from individual elements 104 of the imaging array 102 and sensed at the instrument tip are identical to signals sent from the instrument tip and received by the individual elements of the imaging array).

It is noted that a synthetic aperture transmit scheme could also be used to perform pulse-echo imaging. In that case, as for the synthetic aperture with virtual transducers embodiment, the pulse-echo transmit sequence would not be affected by the tracking schemes.

As an alternative to using one-way only beamforming as in the above-described embodiments, the tracked receiver can be localized with comparable accuracy by focusing at the depth of the receiver. Thus, in FIG. 5, there would be no one-way only beamforming 516. In particular, the ultrasound scanner keeps sending regular imaging (focused) beams. The time from beam emission to reception by the tracked receiver indicates the depth of the receiver, e.g., r(P) in FIG. 1 if the reflector 106 were a receiver. That information is fed back to the ultrasound scanner that sets the transmit focal depth at the depth of the tracked receiver 202 for optimal lateral resolution at that depth. The position of the imaging beam that yields the highest amplitude sensed at the tracked receiver's location corresponds to the lateral (or angular, depending on the imaging geometry) location of the tracked receiver 202.

Figure 6:
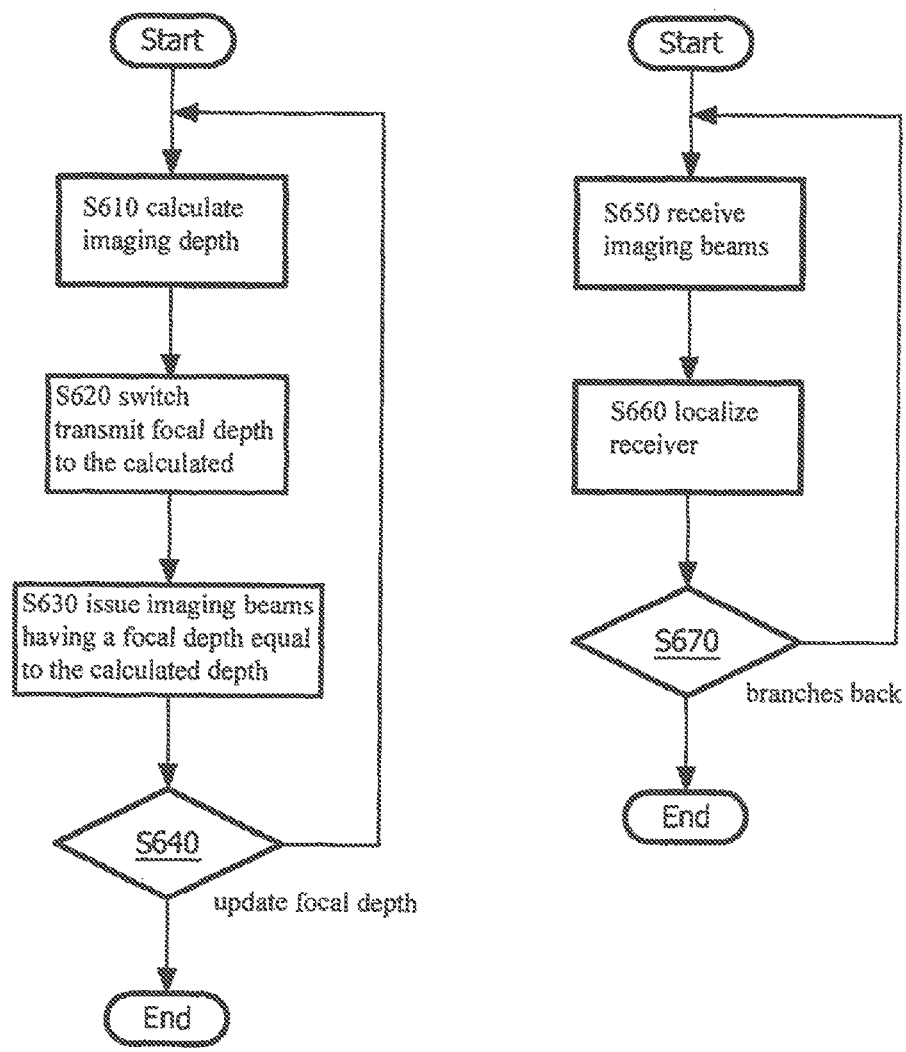
FIG. 6 is a flow chart showing an embodiment in which transmit focal depth is switched to the measured image depth of the receiver.

Referring to FIG. 6, steps which are performed automatically and without user intervention include: calculating, with respect to an ultrasound scanner, an imaging depth of an ultrasound receiver (step S610), switching transmit focal depth to that imaging depth (step S620), and issuing imaging beams (with simultaneously both a tracking function and a pulse-echo imaging function) with that imaging depth as their focal depth (step S630). While imaging and real-time tracking of the receiver 202 continue (step S640), processing returns to step S610 to continually update focal depth in accordance with the then-present position of the tracked receiver 202. Also shown in FIG. 6 is a process in which the imaging beams issued in step S630 are received (step S650) and, from the received beams, the receiver 202 is localized (step S660) and accordingly represented in the displayed image 224 of the region of interest 206. While real-time imaging/tracking continue (step S670), processing branches back to step S650.

The result is a diffraction-limited localization accuracy for the catheter, as with the RDT technique. However, here the transmit focal depth has to be physically modified as the catheter advances.

Figure 7:
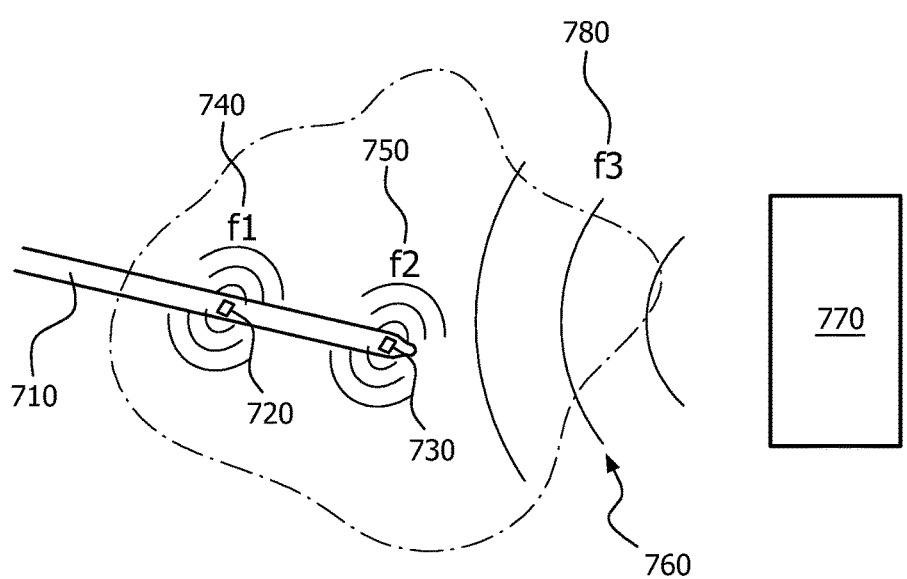
FIG. 7 shows an interventional tool with two embedded transmitters.

FIG. 7 shows an interventional tool 710 with two transmitters 720, 730 attached and located mutually apart. Having two or more transmitters or, alternatively two or more receivers, on the interventional tool 710 allows reliably and precisely identifying the position and orientation of an interventional tool or catheter with respect to the surrounding tissues, which is extremely useful for visualization of the surgical procedure, and often a difficult task using standard ultrasound imaging alone. This affords visualizing and predicting the path of the interventional tool so that major vessels shown, e.g., in Doppler or vessel contrast modes, are reliably and safely avoided during the intervention. The configuration in FIG. 7 of the two transmitters 720, 730 on the interventional tool 710 (or alternatively receivers, as appropriate) is implementable in any of the above-mentioned embodiments of the invention.

As mentioned above, in embodiments other than that for synthetic aperture with virtual transducers, the real-time anatomy or pulse-echo ultrasound is, by frequency band or by timing, kept separate from ultrasound used by the transmitter or receiver in real-time tracking. If by timing, acquisition of tracking frames 422 alternates with acquisition of imaging frames 416. As an alternative for embodiments with transmitters, the separation can be accomplished by frequency band. The transmitters 720, 730 transmit at frequencies f1, f2 640, 650. These are in a frequency band different from that of the pulse-echo ultrasound 760 from an ultrasound scanner 770, which emits ultrasound at frequency f3 780.

In an aspect of the invention, it is an ultrasonic tracking method for reliably and precisely identifying the position of an interventional tool or catheter with respect to the surrounding tissues, which is often a difficult task using standard ultrasound imaging. For instance, according to what is proposed herein, the tip of a biopsy needle can be precisely located, distinguishing it from points along the shaft which are often mistaken for the tip when imaging the needle in traditional pulse-echo B-mode. In addition, ultrasound emission from the tip of the needle or catheter does not require reflection of the beam from the ultrasound scanner, so that the needle or catheter is visible even in cases where the imaging beam would be reflected away from the ultrasound scanner or when the needle or needle is away from the imaging plane. Moreover, the proposed tracking technology will work in all ultrasound imaging modes, including grayscale tissue imaging and contrast and Doppler flow imaging (as discussed hereinabove). With regard to imaging vascularity (e.g., vascular flows and tissue perfusion), all signals from the tissue as well as reflected signals for the catheter or needle are suppressed in contrast imaging mode, so the catheter is invisible in contrast mode. Advantageously, the above-described embodiments of the invention avoid this shortcoming.

The novel tracking methods and devices also overcome the need for electromagnetic tracking of the surgical tool (thereby reducing the amount of equipment to be included in the operating room) and all the associated calculations that have to be done for calibration of tracking and co-registration with intra-operative images. In embodiments of the present invention, the position of the interventional tool is automatically co-registered with intra-operational ultrasound. This new tracking approach is cost effective and conveniently compatible with a large base of ultrasound scanners available in hospitals.

It should be noted that the above-mentioned embodiments illustrate rather than limit the invention, and that those skilled in the art will be able to design many alternative embodiments without departing from the scope of the appended claims. For example, ones of the various methods and devices according to the invention which, as indicated above, are adaptable to either a tracked source or a tracked receiver can be combined into a single embodiment by, for example, repeating methods steps but for the other case, or, for apparatus, providing, in a single device, the elements for implementing both cases. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer having a computer readable storage medium and/or by means of an integrated circuit having a machine-accessible storage medium. The mere fact that certain measures are recited in mutually different dependent claims does not indicate that a combination of these measures cannot be used to advantage.

What is claimed is:

1. A medical system for locating an object comprising:
    an ultrasound imaging device configured to provide imaging beams insonifying a region of interest;
    a receive device configured to receive the imaging beams and being located on the object; and
    a processor configured to process digital signal outputs by the receive device to locate the object in the region of interest;
    wherein the processor has a receive beamformer configured to perform one-way only beamforming of output signals from the receive device.

2. The medical system of claim 1, wherein the processor is configured to process digital signals using at least one of signal processing, beamforming, computer vision and pattern recognition methods.

3. The medical system of claim 1, wherein one-way beamforming includes retrospectively focusing the imaging beams at all depths in the region of interest.

4. The medical system of claim 1, wherein the processor is further configured for use with three-dimensional imaging.

5. The ultrasound device of claim 1, wherein the processor is configured for real-time tracking of the object within the region of interest.

6. A method for locating an object within a region of interest via a medical system comprising acts of:
    with a receive device, detecting one or more imaging beams insonifying the region of interest, the receive device being affixed to the object;
    receiving digital signal outputs by a processor from the receive device;
    processing the digital signal outputs to locate the object in the region of interest, wherein the processing act comprises signal processing of one-way only output signals from the receive device.

7. The method of claim 6, wherein the act of processing the digital signal outputs to locate the object in the region of interest comprises at least one of signal processing, beamforming, computer vision and pattern recognition methods.

8. The method of claim 6, wherein the act of performing one-way only beamforming of output signals from the receive device comprises retrospectively focusing the imaging beams at all depths in the region of interest.

9. The method of claim 6, wherein the region of interest comprises a three-dimensional space.

10. The method of claim 6, wherein the act of processing the digital signal outputs to locate the object in the region of interest comprises real-time tracking of the object within the region of interest.

* * * * *